(12) United States Patent
Livescu et al.

(10) Patent No.: US 9,528,974 B2
(45) Date of Patent: Dec. 27, 2016

(54) FRICTION APPARATUS AND METHOD FOR MEASURING LUBRICITY OF DOWNHOLE FLUIDS

(71) Applicant: BAKER HUGHES INCORPORATED, Houston, TX (US)

(72) Inventors: Silviu Livescu, Calgary (CA); John Delorey, Calgary (CA)

(73) Assignee: Baker Hughes Incorporated, Houston, TX (US)

( * ) Notice: Subject to any disclaimer, the term of this patent is extended or adjusted under 35 U.S.C. 154(b) by 281 days.

(21) Appl. No.: 14/212,570

(22) Filed: Mar. 14, 2014

(65) Prior Publication Data

US 2015/0101399 A1    Apr. 16, 2015

Related U.S. Application Data

(60) Provisional application No. 61/889,741, filed on Oct. 11, 2013.

(51) Int. Cl.
*G01N 33/26* (2006.01)
*G01N 33/30* (2006.01)
*G01N 33/18* (2006.01)
G01N 19/02 (2006.01)
G01N 33/28 (2006.01)

(52) U.S. Cl.
CPC ............. *G01N 33/30* (2013.01); *G01N 33/18* (2013.01); *G01N 19/02* (2013.01); *G01N 33/2823* (2013.01)

(58) Field of Classification Search
CPC ..... G01N 33/30; G01N 33/2823; G01N 19/02

USPC ............................................. 73/53.05, 9, 10
See application file for complete search history.

(56) References Cited

U.S. PATENT DOCUMENTS

| | | | | |
|---|---|---|---|---|
| 3,785,196 A | * | 1/1974 | Smith .................... | G01N 33/30 73/10 |
| 3,913,377 A | * | 10/1975 | Lindeman .............. | G01N 3/567 73/10 |
| 3,939,690 A | * | 2/1976 | Kuss ....................... | G01N 3/56 73/9 |
| 4,458,528 A | * | 7/1984 | Roper ................ | B01D 39/2068 73/152.49 |
| 5,377,525 A | * | 1/1995 | Hutchinson ............ | G01N 33/30 73/10 |
| 5,388,442 A | * | 2/1995 | Kumar ................... | G01N 19/02 73/10 |

(Continued)

FOREIGN PATENT DOCUMENTS

CA          1223458 A1    6/1987

*Primary Examiner* — Lisa Caputo
*Assistant Examiner* — Jonathan Dunlap
(74) *Attorney, Agent, or Firm* — Mossman, Kumar & Tyler, P.C.

(57) ABSTRACT

A lubricity testing apparatus may have a first surface configured for moving against a second surface, a second surface, a measurement device in communication with the first surface, and an actuator in communication with the first surface. A fluid may be circulated about or over at least one of the surfaces. The measurement device may measure at least one force encountered when the first surface moves against the second surface. The actuator may move the first surface against the second surface. At least one force related to the first surface may be measured as the first surface moves against the second surface to determine the lubricity of the fluid.

20 Claims, 2 Drawing Sheets

(56) References Cited

U.S. PATENT DOCUMENTS

| | | | |
|---|---|---|---|
| 5,616,842 A * | 4/1997 | Armengaud | G01N 11/14 73/152.18 |
| 5,795,990 A | 8/1998 | Gitis et al. | |
| 5,969,227 A * | 10/1999 | Kenney | G01N 19/02 73/10 |
| 6,105,415 A * | 8/2000 | Kenney | G01N 19/02 73/10 |
| 6,112,573 A * | 9/2000 | Thelen | G01N 33/30 73/10 |
| 6,324,918 B1 | 12/2001 | Gitis et al. | |
| 6,330,820 B1 * | 12/2001 | Cotterill | G01L 5/288 73/121 |
| 6,418,776 B1 | 7/2002 | Gitis et al. | |
| 6,508,105 B1 * | 1/2003 | Vigneaux | G01N 33/2823 73/10 |
| 6,546,782 B1 * | 4/2003 | De La Cruz | G01N 3/56 73/10 |
| 6,752,001 B1 * | 6/2004 | LaPointe | G01N 19/02 73/10 |
| 6,817,223 B2 * | 11/2004 | Lenz | G01N 19/02 73/10 |
| 6,840,082 B2 * | 1/2005 | Evans | G01N 19/02 73/10 |
| 7,013,713 B2 * | 3/2006 | Webster | G01N 33/30 73/53.06 |
| 7,024,920 B2 * | 4/2006 | Discenzo | G01N 11/00 702/50 |
| 7,228,727 B2 * | 6/2007 | Discenzo | G01N 11/00 702/50 |
| 7,516,650 B2 * | 4/2009 | Discenzo | G01N 11/00 702/50 |
| 7,581,434 B1 * | 9/2009 | Discenzo | G01N 33/2888 73/53.01 |
| 8,739,609 B2 | 6/2014 | Lukay et al. | |
| 9,194,784 B1 * | 11/2015 | Bi | G01N 3/56 |
| 2010/0126252 A1 * | 5/2010 | Bailey | G01N 11/14 73/54.28 |
| 2014/0290330 A1 * | 10/2014 | Blue | G01N 3/567 73/9 |

\* cited by examiner

FRICTION APPARATUS AND METHOD FOR MEASURING LUBRICITY OF DOWNHOLE FLUIDS

CROSS-REFERENCE TO RELATED APPLICATION

This application claims the benefit of Provisional Patent Application No. 61/889,741 filed Oct. 11, 2013, which is incorporated by reference herein in its entirety.

TECHNICAL FIELD

The present invention relates to systems, apparatuses, and methods for determining the lubricity of a fluid by moving a first surface against a second surface where the fluid is circulated about at least one of the surfaces, and a force may be measured related to the first surface as the first surface is moving against the second surface, and the invention more particularly relates to more accurately measuring the lubricity of fluids to be used with respect to coiled tubing strings.

BACKGROUND

Fluids are frequently tested in a laboratory to obtain a rough estimate of the fluid's lubricity before the fluid is used in the oilfield. It is important that the laboratory measurements of lubricity reliably correlate to the lubricity observed in the field. For example, operators depend on reliable lubricity coefficients as input into computer drilling models to predict drillstring loads to optimize casing runs, to enhance the well design with respect to torque and drag, to recommend proper mud systems, determine the optimum lubricant amounts, to develop new lubricant additives, and the like.

Lubricity is a measure of the coefficient of friction between a moving part and a surface in contact with the part. The lower the coefficient of friction, the greater the lubricity. The coefficient of friction, p, is defined as the ratio of the force, F, required to move an object in contact with a surface to the force, $W_1$, pushing downward or perpendicular to the object: $\mu=F/W_1$. The coefficient of friction may alternatively be called the friction coefficient, friction factor, or the lubricity coefficient.

Lubricity of a material cannot be directly measured, so tests are performed to quantify a lubricant or fluid performance. By determining the friction between the surfaces, the lubricity may be determined. For example, the lubricity may be determined by determining how much wear is caused to a surface by a given friction-inducing surface to another surface in a given amount of time under particular conditions, e.g. surface size, temperature, pressure, etc. More wear to a surface indicates a worse lubricity. For this reason, lubricity is also termed a substance's anti-wear property. Non-limiting examples of current apparatuses to test lubricity used by those skilled in the art include "ball-on-cylinder" and "ball-on-three-discs" tests.

A substantial portion of the time required for well intervention operations, drilling operations, completion operations, and/or fracturing operations is consumed in replacing worn metal pieces and/or equipment used for these tasks. Excessively high torque and drag may cause costly delays or interruptions during downhole operations. The metal surfaces also wear down due to frictional forces, resulting in reduced equipment life. These problems generally increase at high temperatures and/or high pressures.

Lubricants or lubricating agents may be added to a fluid to reduce or decrease friction, torque, and/or drag between two surfaces. This may be especially important when one or both surfaces are metal surfaces, such as within and/or around coiled tubing used during coiled tubing operations. Coiled tubing is used in the oil and gas industry for interventions in oil and gas wells, as production tubing in depleted gas wells, and/or for similar operations to wirelining. Chemicals may be pumped through the coiled tubing and may be pushed into the hole instead of relying only on gravity to get the chemicals into the hole. Coiled tubing is a metal piping typically ranging in diameter from about 0.5 inch to about 5 inches depending on the coiled tubing operation.

The fluids may be drilling fluids, completion fluids, fracturing fluids, etc. Drilling fluids are typically classified according to their base fluid. In water-based fluids, solid particles are suspended in a continuous phase including water or brine. Oil can be emulsified in the water, which is the continuous phase. "Water-based fluid" is used herein to include fluids having an aqueous continuous phase where the aqueous continuous phase can be all water or brine, an oil-in-water emulsion, or an oil-in-brine emulsion. Brine-based fluids, of course are water-based fluids, in which the aqueous component is brine.

Oil-based fluids are the opposite or inverse of water-based fluids. "Oil-based fluid" is used herein to include fluids having a non-aqueous continuous phase where the non-aqueous continuous phase is all oil, a non-aqueous fluid, a water-in-oil emulsion, a water-in-non-aqueous emulsion, a brine-in-oil emulsion, or a brine-in-non-aqueous emulsion. In oil-based fluids, solid particles are suspended in a continuous phase including oil or another non-aqueous fluid. Water or brine can be emulsified in the oil; therefore, the oil is the continuous phase. In oil-based fluids, the oil may include any oil or water-immiscible fluid that may include, but is not limited to, diesel, mineral oil, esters, refinery cuts and blends, or alpha-olefins.

Oil-based fluid as defined herein may also include synthetic-based fluids or muds (SBMs), which are synthetically produced rather than refined from naturally occurring materials. Synthetic-based fluids often include, but are not necessarily limited to, olefin oligomers of ethylene, esters made from vegetable fatty acids and alcohols, ethers and polyethers made from alcohols and polyalcohols, paraffinic, or aromatic, hydrocarbons alkyl benzenes, terpenes and other natural products and mixtures of these types.

There are a variety of functions and characteristics that are expected of completion fluids. The completion fluid may be placed in a well to facilitate final operations prior to initiation of production. Completion fluids are typically brines, such as chloride brines, bromide brines, formate brines, but may be any non-damaging fluid having proper density and flow characteristics. Suitable salts for forming the brines include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof.

Chemical compatibility of the completion fluid with the reservoir formation and fluid is key. Chemical additives, such as polymers and surfactants are known in the art for being introduced to the brines used in well servicing fluids for various reasons that include, but are not limited to, increasing viscosity, and increasing the density of the brine. Water-thickening polymers serve to increase the viscosity of the brines and thus retard the migration of the brines into the formation and lift drilled solids from the wellbore. A regular drilling fluid is usually not compatible for completion operations because of its solid content, pH, and ionic composition.

Completion fluids also help place certain completion-related equipment, such as gravel packs, without damaging the producing subterranean formation zones. The completion fluid should be chemically compatible with the subterranean reservoir formation and its fluids.

A fracturing fluid may be injected into a well as part of a stimulation operation. Fracturing fluids may include water, proppant, and a small amount of non-aqueous fluids designed to reduce friction pressure while pumping the fluid into the wellbore. Such fluids often include gels, friction reducers, crosslinkers, and/or breakers to reduce the viscosity of the gel, and surfactants. The type of additive added to the fracturing fluid is selected depending on the needs for improving the stimulation operation and the productivity of the well.

A drill-in fluid may be used exclusively for drilling through the reservoir section of a wellbore successfully, which may be a long, horizontal wellbore. The drill-in fluid may minimize damage and maximize production of exposed zones, and/or facilitate any necessary well completion. A drill-in fluid may be a fresh water or brine-based fluid that contains solids having appropriate particle sizes (salt crystals or calcium carbonate) and polymers. Filtration control additives and additives for carrying cuttings may be added to a drill-in fluid.

A workover fluid is a fluid for repairing or stimulating an existing production well for the purpose of restoring, prolonging or enhancing the production of hydrocarbons. A well intervention operation is any operation carried out on an oil or gas well during or at the end of its productive life that alters the state of the well and/or the well geometry, provides well diagnostics, or manages the production of the well. Such operations may include logging, gauging, plugging, re-perforating, and/or various downhole mechanical operations to reduce flow restrictions when trying to obtain additional production volume from a well.

Therefore, it would be desirable if a lubricity testing apparatus that simulates the conditions under which fluids used for various operations (e.g. coiled tubing operations) function to measure the effectiveness of a lubricant against drag and other frictional resistance forces encountered in such operations. It would also be beneficial for the lubricity testing apparatus to test a fluid under dynamic conditions that are more closely encountered in the field.

SUMMARY

There is provided, in one form, a lubricity testing apparatus having a first surface configured for moving against a second surface, a second surface different from the first surface, a measurement device in communication with the first surface, and an actuator in communication with the first surface. The first surface may be or include, but is not limited to a coiled tubing surface, a wellbore casing surface, a drill string surface, a pipe surface, a drill bit surface, well open hole surface (e.g. rock), and combinations thereof. The measurement device may measure at least one force encountered when the first surface moves against the second surface. The actuator may move one of the surfaces against the other surface.

There is provided, in another non-limiting form, a lubricity testing system that may have or include, but is not limited to, a lubricity testing apparatus, a measurement device in communication with the lubricity testing apparatus, and a user device in communication with the measuring device. The lubricity testing apparatus may have or include, but is not limited to a non-suspended surface configured for moving against a suspended surface, a suspended surface suspended above the non-suspended surface by a suspending device, and an actuator in communication with at least one of the surfaces for moving the surfaces against each other. The measurement device may measure at least one force encountered when the surfaces move against each other. The user device may record the data obtained from the measuring device.

In another non-limiting form, a method is provided for determining the lubricity of a fluid. The method may include moving a first surface against a second surface different from the first surface, and circulating a fluid about at least one of the surfaces where the temperature of the fluid is as high as about 500° C. and where a pressure applied to the fluid is as high as about 10,000 psi. At least one force may be measured related to the first surface as the first surface is moving against the second surface, and the lubricity of the fluid may be determined therefrom. 'Circulating the fluid about at least one of the surfaces' is defined to mean circulating, pouring, pumping, and combinations thereof about the surface(s) so that at least one of the surfaces may have the fluid when contacting the other surface. In a non-limiting embodiment, the fluid may be circulated over at least one of the surfaces; alternatively, the fluid may be circulated between the surfaces, and combinations thereof.

The apparatus, system, and method may be used to test and determine the lubricity of a fluid when the fluid is subjected to typical downhole conditions.

Figure 1:
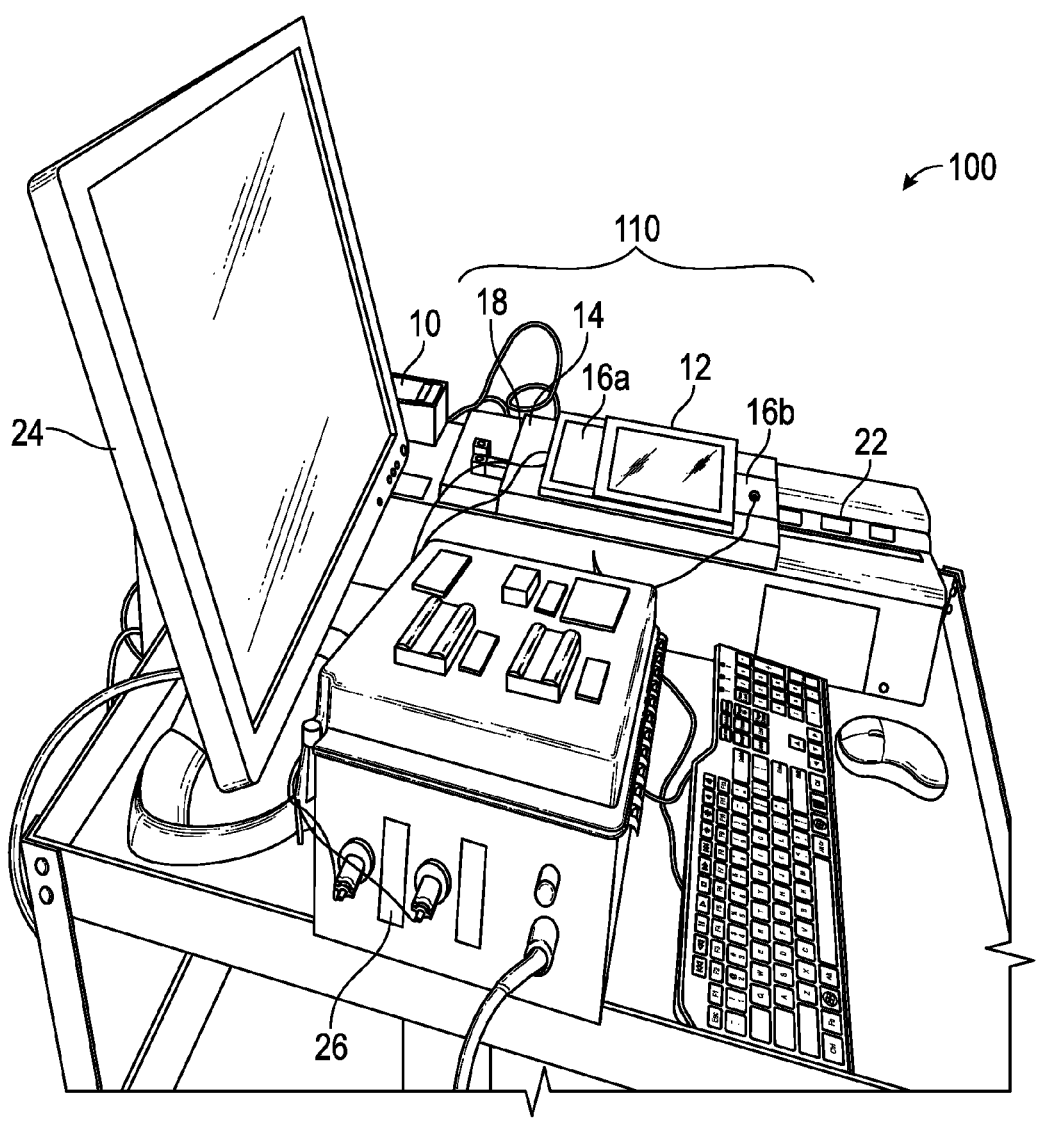
FIG. 1 is an illustration of one non-limiting embodiment of the lubricity testing system.

It will be appreciated that the apparatus illustrated in the Figures are simply one non-restrictive embodiment of the apparatus as described herein, the features of which are not necessarily to scale, and which may be reconfigured in design, orientation and appearance while still being encompassed by the methods and apparatus described and claimed herein.

DETAILED DESCRIPTION

It has been discovered that a lubricity testing apparatus may be used to test and determine the lubricity of a fluid when the fluid is subjected to typical downhole conditions. The lubricity testing apparatus may have a first surface configured for moving against a second surface, a second surface, a measuring device in communication with the first surface for measuring a force encountered when the first surface moves against the second surface, and an actuator in communication with the first surface for moving the first surface against the second surface. The actuator may overcome the frictional force generated by contact between the first surface and the second surface.

A fluid may be circulated about at least one of the surfaces to test the lubricity of the fluid. A user may pour the fluid onto the surface(s), or a fluid pump may be in fluid communication with at least one of the surfaces to circulate a fluid about the surface(s) in a non-limiting embodiment.

To better estimate the lubricity of the fluid under downhole conditions, it may be beneficial for at least one of the surfaces to be a metal surface typically used downhole, such as but not limited to a wellbore casing, a drill string, a pipe, a drill bit, and combinations thereof. Alternatively, at least one of the surfaces may be a rock slate to mimic the coiled tubing movement on open hole rocks. In a non-limiting embodiment, the metal surface or rock slate surface may have solid particles added thereto to simulate sand grains, proppant, and the like between the casing and the coiled tubing and test the effect of such solid particles on the coefficient of friction in such an instance.

The metal and/or rock surface may be 'real' or a simulated version of the metal surface. "Real" surface is defined as being the actual type of surface; whereas, "simulated" surface refers to any surface designed to function the same as the real surface, but is not actually the real surface. In one non-limiting embodiment, a simulated surface may have the same dimensions (e.g. length, width, depth) and/or the same surface roughness to determine a coefficient of friction related to the simulated surface and predict a coefficient of friction for the real surface having the same dimensions and/or surface roughness. "First surface" and "second surface" are used herein to differentiate the surfaces from each other.

As used herein, the first surface may move against the second surface; said differently, the first surface may be actuated by an actuator. The second surface may be stationary, or an actuator may optionally actuate the second surface also. "Moving" is defined herein to include the actions of rolling, sliding, or translating. It will be appreciated that either the first surface or the second surface or both may be moved against the other, and that what is important is that some relative motion is imparted by the actuator so that contact between the two surfaces occurs, but that it is not necessarily critical which of the surfaces is in motion.

The actuator may allow the first surface to move against the second surface by providing kinetic friction to the first surface. The combination of separately controllable translational, rotational, and lateral actions effectively simulates the wide variety of conditions under field conditions (e.g. coiled tubing operations) to allow for accurate determination of the lubricity of the test fluid. Non-limiting examples of actuators may be or include, but are not limited to a rod, a bar, a pipe attached to the first surface, and combinations thereof.

In a non-limiting embodiment, the lubricity testing apparatus may have a first heating element disposed between the first surface and/or the second surface in another non-limiting embodiment. Alternatively, the first heating element may heat the lubricity testing apparatus without directly contacting the apparatus, e.g. the heating element(s) may be in close proximity to the surfaces of the lubricity testing apparatus where the heating element may heat the surface(s), but does not actually contact the surfaces. Non-limiting examples of the heating element(s) may be or include, but are not limited to, a heating pad, a heating wire, a flame, a fluid bath, and combinations thereof. A second heating element may also heat or contact the fluid. Alternatively, the heating element(s) may be applied directly to the lubricity testing apparatus, the fluid, or combinations thereof.

In an alternative embodiment, the lubricity testing apparatus may have a measurement device in communication with the first surface for measuring a force encountered when the first surface moves against the second surface. The measurement device may be separate from the lubricity testing apparatus, or the measuring device may be disposed on or in contact with one or both of the surfaces. In one non-limiting embodiment, the first surface and/or the second surface may have a sensor disposed thereon that sends data to a user device for recording the measurement data. Non-limiting examples of the measuring device or measurement sensors may be or include but are not limited to mechanical force gauges, electrical force gauges, digital force gauges, torque force gauges, etc.

In a non-limiting embodiment, the lubricity testing apparatus may have at least a first temperature sensor. The first temperature sensor may be disposed on at least one of the surfaces, or another portion of the lubricity testing apparatus. Non-limiting examples of the temperature sensor(s) may be or include but is not limited to a thermocouple. Alternatively, the first heating element may include the first temperature sensor. In yet another non-limiting embodiment, the measurement device may have or include the first temperature sensor. The first temperature sensor may be in contact with the fluid, or an optional second temperature sensor may also be located on or in the fluid pump to monitor the fluid temperature.

In yet another non-limiting embodiment, the lubricity testing apparatus may be in communication with a user device, such as but not limited to, a computer, a laptop, a smart phone, an electronic tablet (e.g. an iPad™), a microcontroller, and combinations thereof. A user device may record data, generate data and/or reports, calculate the lubricity of the test fluid, calculate the coefficient of friction, and/or perform other analytical and control functions related to the lubricity testing apparatus.

A fluid may be circulated about at least one of the surfaces, while the first surface moves against the second surface, and a force related to the first surface may be measured. A non-limiting example of the force that may be measured is the friction coefficient, also known as the coefficient of friction or lubricity coefficient. The lubricity of the fluid may be determined from the measurement of the friction, such as an inverse of the coefficient of friction in one non-limiting example.

The fluid may be used as an integral component of existing downhole fluid formulations. The fluid may be a water-based downhole fluid, an oil-based fluid, and mixtures thereof. The phrase "water-based" or "aqueous-based" includes any downhole fluid comprising water or a water-based solution as the continuous phase, including oil-in-water and oil-in-brine emulsions. The phrase "oil-based" includes any downhole fluid comprising oil or an oil-based fluid as the continuous phase, including water-in-oil emulsions, brine-in-oil emulsions, and the like. Any of these fluids may contain a lubricant. The fluid may be a lubricant per se, a lubricant mixed with a downhole fluid, a downhole fluid, and the like. The fluid may form a coherent lubricating film on at least the first surface, and a lubricating film may form on additional surfaces as needed, once the fluid is circulated about at least the first surface.

In one non-limiting embodiment, the amount of the lubricant to mix into a downhole fluid may be calculated based on the average roughness of the first surface and/or the second surface. For example, if the average roughness of the coiled tubing string and the well casing are 8 µm and 12 µm, respectively, the lubricant may adhere to the surfaces and completely cover all of their asperities. Assuming that 90% of the mixed lubricant remains dispersed in the total downhole fluid, and knowing the well and coiled tubing string geometry (diameter and length), the minimum amount of lubricant may be calculated as follows in one non-limiting embodiment:

$$X_{min} = \frac{4 \times (8 \ \mu m \times d_{CT} + 12 \ \mu m \times d_{in})}{10\% \times (d_{in}^2 - d_{CT}^2)}$$

where $d_{CT}$ and $d_{in}$ are the external and internal diameter of the coiled tubing string and well casing, respectively. For example, for a 2 inch coiled tubing string and a 5.5 inches internal diameter casing, the minimum concentration of lubricant in the downhole fluid according to the formula would be about 0.5%.

The downhole fluid may include an effective amount of the lubricant to form a lubricating film on at least one surface. In a non-limiting example, the amount of the lubricant within the downhole fluid may range from about 0.2 vol % independently to about 10 vol % of the total downhole fluid, alternatively from about 0.4 vol % independently to about 7 vol % in another non-limiting embodiment. The amount of fluid to be tested with the lubricity testing apparatus may range from about 1 milliliter (mL) independently to about 500 mL, or from about 10 mL independently to about 100 ml in a non-limiting embodiment. As used herein with respect to a range, "independently" means that any threshold may be used together with another threshold to give a suitable alternative range, e.g. about 0.2 vol % independently to about 0.4 vol % is also considered a suitable alternative range for the amount of the lubricant within the downhole fluid.

The downhole fluid may be or include, but is not limited to, a well intervention fluid, a drilling fluid, a completion fluid, a fracturing fluid, a drill-in fluid, a workover fluid, and combinations thereof. In a non-limiting embodiment, the fluid may be water or a water-based fluid, e.g. seawater. The fluid may have or include polymers capable of viscosifying the fluid and/or providing filtration control for the fluid, e.g. a drilling fluid. The polymers may be non-toxic, and the type of polymers may depend upon the base fluid of the downhole fluid. To further simulate downhole conditions, the fluid may have a pH ranging from about 9 independently to about 12; alternatively, the pH of the fluid (e.g. a completion fluid, a well intervention fluid, etc.) may be less than 9, or range from about 6 independently to about 9 in a non-limiting embodiment.

An acidic fluid, such as an acidic completion fluid, may include the lubricant and have a pH ranging from about 0 independently to about 5 in another non-limiting embodiment. The pH of the fluid may be adjusted with a suitable alkaline material, including but not necessarily limited to alkali metal hydroxides and alkali metal acetates. The alkali metal acetates may be or include, but are not necessarily limited to, sodium acetate and potassium acetate. The alkali metal hydroxides may be or include, but are not necessarily limited to, sodium hydroxide and potassium hydroxide.

The fluid may include conventional additives used in a downhole fluid, such as but not limited to shale stabilizer(s), filtration control additive(s), suspending agent(s), dispersant(s), thinner(s), anti-balling additive(s), other types of lubricant(s), weighting agent(s), seepage control additive(s), lost circulation additive(s), penetration rate enhancer(s), corrosion inhibitor(s), acid(s), base(s), buffer(s), scavenger(s), gelling agent(s), soluble salts, biocides; one or more bridging and/or weighting agents may be added to the fluid, and combinations thereof. Suitable shale stabilizers include, but are not necessarily limited to glycols, inorganic salts, and encapsulating polymers, such as PHPA or acrylamide copolymers, alone or in aqueous solutions, and mixtures thereof. Suitable shale stabilizing inorganic salts include, but are not necessarily limited to alkali metal salts.

The lubricity testing apparatus allows for a better prediction of the coefficient of friction of the fluid when used in field conditions. Such a prediction is important because it may determine whether a thinner diameter of coiled tubing (CT) may be used for a CT operation. A thinner diameter of the coiled tubing would greatly reduce the cost associated with such an operation. In one non-limiting example, a coiled tubing operation that typically uses a 2⅜ inch coiled tubing may be reduced to 2 inches coiled tubing upon determining the lubricity of a particular fluid when properly measured for downhole conditions.

When using the lubricity testing apparatus, the apparatus may be calibrated with the weight of the first surface and the second surfaces, the known roughness measurements of each surface, and coefficient of friction measurements of each surface. These measurements may be used to determine the lubricity of the fluid when circulated about, over, or on the surfaces.

Now turning to the Figures, FIG. 1 is an illustration of an embodiment of the lubricity testing system 100 having a lubricity testing apparatus 110 may be attached to or in communication with a user device 24. The lubricity testing apparatus may be attached to or in communication with a measuring device 10. The lubricity testing apparatus may have a first surface 12 that moves against a second surface 18. Here, a first heating element 14 (e.g. a heating pad) is shown between the first surface 12 and the second surface 18. However, the first heating element 14 may be disposed differently with reference to the lubricity testing apparatus 110, as long as the heat from the first heating element 14 contacts the apparatus 110.

Here, the first temperature sensor 16a measures the temperature at a first end of the first surface 12, and a second temperature sensor 16b measures the temperature at a second end of the first surface 12. A leveling instrument 22 may be used to insure the first surface 12 is at a particular angle, e.g. relatively horizontal, in one non-limiting instance. In addition, an instrument panel 26 and/or the user device 24 may control the measuring device 10 and temperature sensors 16a, 16b.

The lubricity testing apparatus 110 may be enclosed (not shown), in a non-limiting instance. The enclosure may be connected to a pressure pump (not shown) that allows the pressure within the enclosure to be monitored and optionally varied when desired. The internal temperature may also be monitored within the enclosure by a first temperature sensor 12 and optionally varied when desired. The enclosure may be in fluid communication with an optional fluid pump (not shown) where the optional fluid pump may pump fluid into the enclosure. Enclosing the lubricity testing apparatus allows for better monitoring of the temperature and/or pressure of the fluid and/or surfaces and may prevent the fluid from evaporating when testing fluids at high temperature and/or pressures. The optional heating element(s) 14 may or may not be enclosed within the enclosure.

The temperature of the fluid and/or the surfaces may be as high as about 500° C., alternatively from about 10° C. independently to about 350° C., or from about 20° C. independently to about 120° C. in another non-limiting embodiment. The temperature may be held constant within these ranges or vary within these ranges. The pressure of the environment surrounding the fluid and/or the first surface 12 may be as high as about 10,000 psi, alternatively from about 100 psi independently to about 8000 psi, or from about 200 psi independently to about 2000 psi. The pressure may be held constant within these ranges or vary within these ranges.

The first surface 12 may be attached to or in communication with an actuator (not shown) for moving the first surface 12 against the second surface 18. Alternatively, both the first surface 12 and the second surface 18 may be attached or in communication with an actuator, or they may each have their own actuator. The first surface 12 may move at a constant speed ranging from about 10 mm/sec independently to about 10 m/sec, alternatively from about 100 mm/sec independently to about 2 m/sec. Alternatively, the speed may be varied within these speed ranges, such as a stop-start interval having same intervals, a stop-start interval having varied intervals, and/or where the speed is otherwise varied according to a testing protocol.

Figure 2:
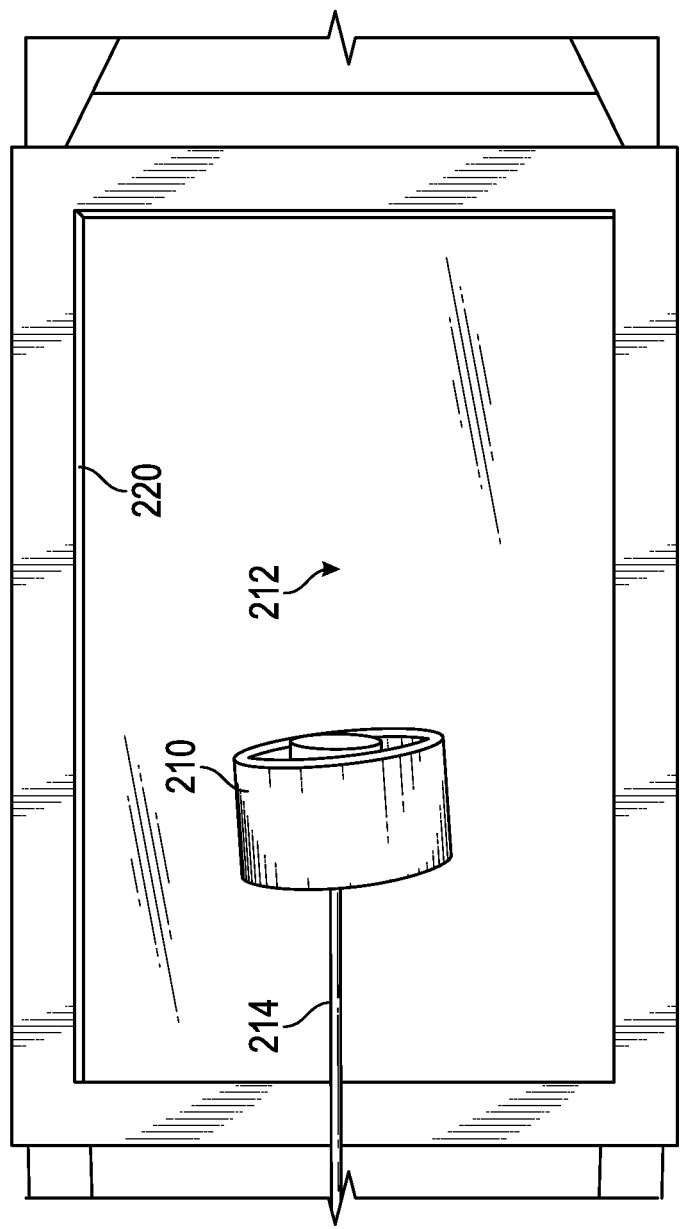
FIG. 2 is an illustration of an alternative embodiment of a suspended surface above a non-suspended surface configured to move against each other.

FIG. 2 is an illustration of an alternative embodiment of the lubricity testing apparatus. Here, a suspended surface 210 is a heated steel sample, and a non-suspended surface 212 is a portion of a coiled tubing coupon for testing the lubricity of a fluid between the suspended surface 210 and the non-suspended surface 212. The suspended surface 210 may be suspended by a suspending device 214, such as a bar, hook, rod, etc. above the non-suspended surface 212.

The suspending device 214 allows for testing a variety of surfaces capable of being suspended, and/or allows the suspended surface 210 to be easily replaced. In one non-limiting embodiment, the suspending device 214 may include a measuring sensor/device, a temperature sensor, a weight sensor, or another sensor type to measure a different parameter associated with the suspended surface 210. For example, the suspending device 214 may have an internal gauge as a measuring device to measure and record the real-time force within the suspending device 214. In a non-limiting embodiment, the measurement device may be mechanically attached and/or magnetically coupled to the suspending surface and/or the non-suspending surface. Likewise, the suspending device may have an internal gauge as a temperature sensor to measure and record the real-time temperatures. The data from the internal gauge may be sent to the user device 24 (FIG. 1) for calculating the coefficient of friction according to $p=F/W_1$ and/or the lubricity of the fluid.

In an alternative non-limiting embodiment, the suspended surface 210 may be configured to move or roll against the non-suspended surface 212. The non-suspended surface 212 may be stationary or actuated to move against the suspended surface. In another non-limiting embodiment, the suspending device 214 may function as an actuator for moving the suspended surface 210 against the non-suspended surface 212. In other words, the 'first surface' may be either the suspended surface 210, or the non-suspended surface 212. One or both surfaces may be in communication with or actuated by an actuator for moving the surface(s).

In a non-limiting embodiment, the first surface 12 may have some form of barrier mechanism 220 around the perimeter of the first surface 12 for keeping the fluid on the second surface 18. Such a barrier 220 may be double-sided scotch tape, metal, plastic, etc.

In the foregoing specification, the invention has been described with reference to specific embodiments thereof, and has been described as effective in providing methods and compositions for determining the lubricity of a fluid. However, it will be evident that various modifications and changes can be made thereto without departing from the broader spirit or scope of the invention as set forth in the appended claims. Accordingly, the specification is to be regarded in an illustrative rather than a restrictive sense. For example, specific surfaces, fluid pumps, fluids, lubricants, actuators, temperatures sensors, heating elements, measurement devices, and user devices falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the lubricity testing apparatus may consist of or consist essentially of a first surface configured for moving against a second surface, a second surface different from the first surface, a measurement device in communication with the first surface, and an actuator in communication with the first surface.

The lubricity testing system may consist of or consist essentially of a lubricity testing apparatus, a measurement device in communication with the lubricity testing apparatus, and a user device in communication with the measuring device; the lubricity testing apparatus may comprise, consist essentially of or consist of a non-suspended surface configured for moving against a suspended surface, a suspended surface suspended above the non-suspended surface by a suspending device, and an actuator in communication with at least one of the surfaces for moving the surfaces against each other.

The method for determining the lubricity of a fluid may consist of or consist essentially of moving a first surface against a second surface different from the first surface, circulating a fluid about at least one of the surfaces where the temperature of the fluid is as high as about 500° C. and where a pressure applied to the fluid is as high as about 10,000 psi, measuring a force related to the first surface as the first surface is moving against the second surface, and determining the lubricity of the fluid.

The words "comprising" and "comprises" as used throughout the claims, are to be interpreted to mean "including but not limited to" and "includes but not limited to", respectively.

What is claimed is:

1. A lubricity testing apparatus comprising:
   a first surface configured for moving against a second surface, wherein the first surface is a real or simulated coiled tubing surface;
   a second surface different from the first surface, wherein the second surface is a real or simulated surface selected from the group consisting of a well casing and a well completion;
   a measurement device in communication with the first surface for measuring at least one force encountered when the first surface moves against the second surface; and
   an actuator in communication with the first surface for moving one of the surfaces against the other surface.

2. The apparatus of claim 1, further comprising a first heating element disposed between the first surface and the second surface.

3. The apparatus of claim 2, wherein the first heating element comprises a first temperature sensor.

4. The apparatus of claim 1, further comprising a fluid pump in fluid communication with at least one of the surfaces.

5. The apparatus of claim 1, further comprising a first temperature sensor disposed on at least one of the surfaces.

6. The apparatus of claim 1, wherein the measurement device contacts the first surface, the second surface, and combinations thereof.

7. The apparatus of claim 1, wherein the first surface is selected from the group consisting of a suspended surface, a non-suspended surface, and combinations thereof.

8. The apparatus of claim 1, wherein the measurement device further comprises at least one sensor selected from the group consisting of a temperature sensor, a weight sensor, a speed sensor, and combinations thereof.

9. A lubricity testing system comprising:
a lubricity testing apparatus comprising:
   a non-suspended surface configured for moving against a suspended surface;
   a suspended surface suspended above the non-suspended surface by a suspending device; and
   an actuator in communication with at least one of the surfaces configured for moving the surfaces against each other;
where the non-suspended surface is a coiled tubing surface and
where the suspended surface is selected from the group consisting of a well casing and a well completion; and
a measurement device in communication with the lubricity testing apparatus for measuring at least one force encountered when the surfaces move against each other; and
a user device in communication with the measuring device to record data obtained from the measuring device.

10. The system of claim 9, further comprising a first heating element in contact with the lubricity testing apparatus.

11. The system of claim 9, further comprising a fluid pump in fluid communication with the lubricity testing apparatus.

12. The system of claim 9, wherein the suspending device comprises the measurement device.

13. The system of claim 9, wherein the suspending device further comprises at least one sensor selected from the group consisting of a temperature sensor, a weight sensor, a speed sensor, and combinations thereof.

14. The system of claim 9, wherein the lubricity testing apparatus further comprises a first temperature sensor disposed on at least one of the surfaces.

15. The system of claim 9, wherein the measurement device further comprises at least one sensor selected from the group consisting of a temperature sensor, a weight sensor, a speed sensor, and combinations thereof.

16. A method for determining the lubricity of a fluid comprising:
moving a first surface against a second surface different from the first surface, where the first surface is a real or simulated coiled tubing surface and the second surface is a real or simulated surface selected from the group consisting of a well casing and a well completion;
circulating a fluid about at least one of the surfaces, wherein the temperature of the fluid is as high as about 500° C.;
measuring at least one force related to the first surface as the first surface is moving against the second surface; and
determining the lubricity of the fluid from the at least one measured force.

17. The method of claim 16, wherein an apparatus is enclosed within an enclosure, where the apparatus comprises the first surface, the second surface, and the fluid, where in the method the fluid would evaporate and where the method further comprises applying a pressure to the fluid as high as about 10,000 psi, and the method further comprises reducing an amount of evaporated fluid as compared to an otherwise identical fluid absent the enclosure.

18. The method of claim 16 where surface roughness of the first surface and/or the second surface are specified.

19. The method of claim 16 where the first surface and/or the second surface has a surface roughness, and where the method further comprises predicting a coefficient of friction for the surface.

20. The method of claim 16 where the first surface and/or the second surface is a simulated surface with a surface roughness the same as a real surface, and where the method further comprises predicting a coefficient of friction for the real surface.

* * * * *